(12) United States Patent
Sayer et al.

(10) Patent No.: US 7,498,043 B2
(45) Date of Patent: Mar. 3, 2009

(54) SILICON SUBSTITUTED OXYAPATITE

(75) Inventors: Michael Sayer, Kingston (CA); Joel Reid, Kingston (CA); Timothy J. N. Smith, Kingston (CA); Jason Hendry, Kingston (CA)

(73) Assignee: Warsaw orthopedic, inc., Warsaw, IN (US)

( * ) Notice: Subject to any disclaimer, the term of this patent is extended or adjusted under 35 U.S.C. 154(b) by 457 days.

(21) Appl. No.: 11/088,094

(22) Filed: Mar. 24, 2005

(65) Prior Publication Data

US 2005/0244449 A1  Nov. 3, 2005

Related U.S. Application Data

(60) Provisional application No. 60/559,956, filed on Apr. 7, 2004.

(51) Int. Cl.
*A61K 9/14* (2006.01)
*A61K 33/42* (2006.01)
*A61K 33/00* (2006.01)
*A61F 2/00* (2006.01)
*A01N 59/26* (2006.01)
*A01N 59/00* (2006.01)

(52) U.S. Cl. .............. 424/426; 424/489; 424/601; 424/602; 424/724

(58) Field of Classification Search ............... None
See application file for complete search history.

(56) References Cited

U.S. PATENT DOCUMENTS

| | | | |
|---|---|---|---|
| 4,668,295 A | * | 5/1987 | Bajpai ............... 106/690 |
| 4,861,733 A | | 8/1989 | White |
| 6,024,085 A | | 2/2000 | Hodge et al. |
| 6,203,574 B1 | * | 3/2001 | Kawamura ............ 623/16.11 |
| 6,312,468 B1 | | 11/2001 | Best et al. |
| 6,323,146 B1 | | 11/2001 | Pugh et al. |
| 6,387,414 B1 | | 5/2002 | Akasi et al. |
| 6,426,114 B1 | | 7/2002 | Troczynski et al. |
| 6,582,672 B1 | | 6/2003 | Bonfield et al. |
| 6,585,946 B1 | | 7/2003 | Bonfield et al. |
| 6,596,338 B2 | | 7/2003 | Scott et al. |

FOREIGN PATENT DOCUMENTS

EP  0 297 595 A  1/1989

OTHER PUBLICATIONS

Gille et al. (International Orthopaedic 2002, 26, 203-206).*
Bayraktar D et al: "Chemical preparation of carbonated calcium hydroxyapatite powders at 37<o>C in urea-containing synthetic body fluids".
Journal of the European Ceramic Society, Elsevier Science Publishers, Barking, Essex, GB, vol. 19, No. 13-14, Oct. 1999, pp. 2573-2579, XP004183803 ISSN:0955-2219, p. 2573, col. 2.
Ruys et al., 119. Silicon-Doped Hydroxyapatite, J. Aust. Ceram. Soc. 29(1/2) pp. 71-80.
Kim et al., 2002 (Biomaterials, 24, 1389-98).
Bonfield et al., 1999 (J. Biomed Matr Res. Mar 15;44(4):422-8).
Sayer et al., 2003 (Structure and composition of Silicon-stabilized tricalcium Phosphate, Biomaterials, 24; 369-382).

* cited by examiner

*Primary Examiner*—Johann Richter
*Assistant Examiner*—Ernst V Arnold
(74) *Attorney, Agent, or Firm*—Gregory Scott Dorland

(57) ABSTRACT

The invention is a silicon substituted oxyapatite compound (Si—OAp) for use as a synthetic bone biomaterial either used alone or in biomaterial compositions. The silicon substituted oxyapatite compound has the formula $Ca_5(PO_4)_{3-x}(SiO_4)_xO_{(1-x)/2}$, where $0<x<1.0$.

30 Claims, No Drawings

SILICON SUBSTITUTED OXYAPATITE

RELATED APPLICATIONS

This application claims priority to U.S. provisional application Ser. No. 60/559,956.

FIELD OF THE INVENTION

The invention relates to synthetic bone biomaterials. More specifically, the present invention relates to silicon substituted oxyapatite (Si—OAp) for use as a synthetic bone biomaterial and a method for the making thereof. The Si—OAp can be used alone or in biomaterial compositions.

BACKGROUND OF THE INVENTION

Calcium phosphates, in particular calcium hydroxyapatite ($Ca_5(PO_4)_3OH$) and other hydroxyapatite materials, are known for use as skeletal reconstitution materials. Various hydroxyapatite materials are disclosed for example in U.S. Pat. Nos. 4,861,733, 6,024,985, 6,387,414, 6,426,114, 6,582,672, 6,585,946 and 6,596,338.

Silicon substituted hydroxyapatite and tricalcium phosphate materials are also known. Ruys et al., 1993 (Silicon-Doped Hydroxyapatite, J. Aust. Ceram. Soc. 29(1/2) pp 71-80) discloses a silicon substituted hydroyxyapatite material. Kim et al., 2003 (Biomaterials, 24, 1389-98) discloses a silicon and magnesium substituted hydroxyapatite material. Bonfield et al., 1999 (J. Biomed Mater Res. Mar 15; 44(4): 422-8) discloses a silicon-substituted hydroxyapatite prepared by a precipitation technique. Sayer et al., 2003 (Structure and composition of silicon-stabilized tricalcium phosphate, Biomaterials, 24; 369-382) discloses a silicon-stabilized tricalcium phosphate material for use in skeletal tissue repair. U.S. Pat. No. 6,312,468 discloses a silicon-substituted apatite that can be converted upon heating to a silicon-substituted hydroxyapatite comprising between 0.1% to 5% by weight of silicon for use as a synthetic bone material. The silicon-substituted hydroxyapatite is stated to be free of calcium oxide and/or tricalcium phosphate.

Oxyapatites are also known and often used in restorative materials for orthopedic and dental applications.

The Applicant has now identified a novel compound, silicon substituted oxyapatite (Si—OAp) that has wide use as a synthetic bone biomaterial compound in a variety of orthopedic applications such as skeletal implants.

SUMMARY OF THE INVENTION

The Applicant has identified a novel silicon substituted oxyapatite (Si—OAp) compound that can be used alone or provided as a composition for use as a synthetic bone biomaterial in a variety of orthopedic applications.

According to an aspect of the invention is a silicon substituted oxyapatite compound referred to herein as "Si—OAp".

According to another aspect of the present invention is silicon substituted oxyapatite (Si—OAp) having the formula $Ca_5(PO_4)_{3-x}(SiO_4)_xO_{(1-x)/2}$, where $0<x<1.0$.

According to another aspect of the present invention is a synthetic biomaterial composition comprising silicon substituted oxyapatite (Si—OAp).

According to still another aspect of the present invention is a synthetic biomaterial composition comprising silicon substituted oxyapatite (Si—OAp) having the formula $Ca_5(PO_4)_{3-x}(SiO_4)_xO_{(1-x)/2}$, where $0<x<1.0$.

According to yet another aspect of the present invention is a method for making silicon substituted oxyapatite (Si—OAp) of the formula $Ca_5(PO_4)_{3-x}(SiO_4)_xO_{(1-x)/2}$, where $0<x<1.0$, said method comprising:

mixing a calcium phosphate colloidal suspension with a finely dispersed, fumed silica while maintaining a ratio of Ca/(P+Si) at about 1.67 in said mixture; and sintering for about 1 hour at a temperature of about 1000° C. to about 1200° C. under vacuum. In aspects, the temperature is about 1175° C. and the vacuum pressure is about $5\times10^{-4}$ torr to about $1\times10^{-5}$ torr.

In the method, the concentration of silicon should be sufficient to substantially remove OH⁻ from the lattice, without causing the apatite structure to collapse to silicocarnotite ($Ca_5(PO_4)_2SiO_4$). The concentration of silicon required falls in a range between about 0.5 mol $SiO_2$: mol HA and about 1.5 mol $SiO_2$: mol HA, or about 2.6 to 7.1 wt % silicon.

In aspects of the invention, the silicon substituted oxyapatite compound (Si—OAp) may be used alone or as a composition for the treatment of a variety of a variety of conditions selected from the group consisting of orthopedic, maxillofacial and dental applications. The compound may be used in vitro, ex vivo and in vivo.

According to another aspect of the present invention is a method for the treatment of orthopedic, maxillo-facial and dental defects, the method comprising providing a silicon substituted oxyapatite compound (Si—OAp) where the compound is provided as a fine or coarse powder, pellets, three-dimensional shaped pieces, macroporous structures, thin films and coatings to said defect.

According to yet another aspect of the present invention is a method for substituting natural bone at sites of skeletal surgery in human and animal hosts with a silicon substituted oxyapatite compound (Si—OAp), the method comprising the steps of:

implanting said silicon substituted oxyapatite compound (Si—OAp) at the site of skeletal surgery wherein such implantation promotes the formation of new bone tissue at the interfaces between the compound and said host.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION OF THE PREFERRED EMBODIMENTS

The Applicants have now identified and characterized a novel compound which is silicon substituted oxyapatite (Si—OAp). This compound is represented by the formula $Ca_5(PO_4)_{3-x}(SiO_4)_xO_{(1-x)/2}$, where $0<x<1.0$. The Si—OAp compound of the invention has various uses in orthopedic, maxillo-facial and dental applications. The Si—OAp compound is biocompatible with cells and tissues in vitro and in vivo and provides a substrate for the synthesis of mineralized matrix thereon by osteoblasts. As such the compound has several applications to repair and promote bone growth.

The silicon substituted oxyapatite compound (Si—OAp) of the invention can be made synthetically or alternatively isolated from a mixture of calcium phosphate phases.

In the Si—OAp compound, silicon substitutes for phosphorous and the OH⁻ is progressively removed from the lattice to charge compensate for the silicon substitution. More generally, starting from a hydroxyapatite composition, the phosphorous is partially substituted with silicon and the hydroxide is removed. Initially OH⁻ is removed as a method of charge compensation for silicon $Si^{4+}$ substitution into phosphorus $P^{5+}$ sites. This is particularly effective in the case when OH⁻ charge compensation occurs near highly localized concentrations of silica such as its addition as a particulate species $SiO_2$ such as Cab-o-Sperse™ or at a macroscopic $SiO_2$:hydroxyapatite interface. During sintering, silicon diffuses throughout the lattice to an equilibrium distribution having a lower concentration of silicon $Si^{4+}$ substituted at $P^{5+}$ tetrahedral sites. Pairs of hydroxide sites in the c-axis OH—channel of the apatite structure will be re-filled by oxygen, $O^{2-}$ while still maintaining the required level of charge compensation. This leads to the formation of the silicon-substituted oxyapatite structure (i.e. Si—OAp compound). While not essential in principle to the method of producing silicon substituted oxyapatite, the introduction of $SiO_2$ which by particulate dispersions leads to an initial non-uniform distribution of $SiO_2$ is of benefit to the creation of an oxyapatite structure without collapse of the structure to undesirable silicocarnotite.

The Si—OAp compound of the invention can be used alone fabricated as a fine or coarse powder, pellets, three-dimensional shaped pieces, macroporous structures, thin films and coatings. Alternatively, the Si—OAp compound can be fabricated into a composition which may additionally comprise one or more calcium compounds such as but not limited to oxyapatite, hydroxyapatite, calcium hydroxyapatite, tricalcium phosphate, calcium oxide, alpha-tricalcium phosphate and beta-tricalcium phosphate.

To the Si—OAp compound or composition of the invention, additional materials may be added for increasing properties such as strength or for application of agents in a time release manner. Such materials may include but are not limited to one or more of a bioresorbable polymer which may be one or a combination of collagen, poly-lactic acid (PLA), poly-glycolic acid (PGA), copolymers of lactic acid and glycolic acid (PLGA), chitosan, chitin, gelatin, or any other resorbable polymer. The polymer material can be used alone, may be reinforced with a particulate form of the Si—OAp compound or Skelite™ compound (described in U.S. Pat. No. 6,323,146, the disclosure of which is incorporated herein in its entirety) or other particulate compound or fibrous biocompatible material as is understood by one of skill in the art. Such a Si—OAp composite may contain a biological agent known to induce bone formation as is discussed below. The polymeric material will resorb as the host bone grows into the interstices to replace it.

The compositions of the present invention incorporating the Si—OAp compound can be used as carriers and thus concomitantly with other agents (as discussed above) for treating bone diseases. Examples of drugs concomitantly used may include for example, calcium preparations (e.g. calcium carbonate), calcitonin preparations, sex hormones (e.g. estrogen, estradiol), prostaglandin A1, bisphosphonic acids, ipriflavones, fluorine compounds (e.g. sodium fluoride), vitamin K, bone morphogenetic proteins (BMPs), fibroblast growth factor (FGF), platelet-derived growth factor (PDGF), transforming growth factor (TGF-β), insulin-like growth factors 1 and 2 (IGF-1, 2), endothelin, parathyroid hormone (PTH), epidermal growth factor (EGF), leukemia inhibitory factor (LIP), osteogenin, and bone resorption repressors such as estrogens, calcitonin and biphosphonates. In aspects of the invention, the Applicant's own bone and cartilage stimulating peptides (BCSPs) may be used in Si—OAp compositions as these peptides stimulate the development, maintenance and repair of bone, cartilage and associated connective tissue. Such BCSP's are described in the Applicant's PCT CA03/00634 (the disclosure of which is incorporated herein in its entirety). Briefly, BCSP peptides comprise an amino acid motif selected from the group consisting of "PG", "GP", "PI" and "IG" and have up to 10 amino acids upstream and/or downstream of the amino acid motif. The "P" in the motif represents either proline or hydroxyproline. More specifically, these BCSP peptides peptide have a formula selected from the group consisting of:

$$X—(P_1)_m Gly(P_2)_n, \qquad (I)$$

$$(P_1)_m Gly(P_2)_n\text{-}Z \text{ and} \qquad (II)$$

$$X—(P_1)_m Gly(P_2)_n\text{-}Z;$$

wherein $P_1$ and $P_2$ are selected from the group consisting of proline and hydroxyproline, m=0 or 1, n=0 or 1, where m and n are independently selected;

wherein X is selected from the group consisting of leucine, glycine-leucine, proline-isoleucine, glycine-proline-isoleucine, asparagine-glycine-leucine and proline-glycine-proline-isoleucine-glycine-proline; and wherein Z is selected from the group consisting of isoleucine, arginine, isoleucine-glycine, isoleucine-glycine-proline, isoleucine-glycine-hydroxyproline, isoleucine-glycine-proline-proline, isoleucine-glycine-proline-proline-glycine, isoleucine-glycine-proline-proline-glycine-proline, isoleucine-glycine-proline-proline -glycine-proline-arginine, isoleucine-glycine-proline-proline-glycine-proline-arginine -glycine-arginine-threonine-glycine-aspartate-alanine and arginine-glycine-arginine -threonine-glycine-aspartate-alanine.

The invention also contemplates mixtures of such agents and drugs as described supra for example, may also be used and formulated within the compositions of the present invention or used in conjuction with the compositions of the present invention.

In one embodiment, the Si—OAp compound of the invention may be used in conjunction with a synthetic biomaterial compound (Skelite™, described in Applicant's U.S. Pat. No. 6,323,146 and herein incorporated by reference). Briefly, Skelite™ is an isolated bioresorbable biomaterial compound comprising calcium, oxygen and phosphorous, wherein a portion of at least one of these elements is substituted with an element having an ionic radius of approximately 0.1 to 0.6 Angstroms. More specifically, Skelite™ has the formula: $(Ca)_i\{(P_{1-x-y-z}B_x C_y D_z)O_j\}_2$ wherein B, C and D are selected from those elements having an ionic radius of approximately 0.1 to 0.4 Angstroms; x is greater than or equal to zero but less than 1; y is greater than or equal to zero but less than 1; z is greater than or equal to zero but less than 1; x+y+z is greater than zero but less than 1; i is greater than or equal to 2 but less than or equal to 4; and j is equal to 4−δ, where δ is greater than or equal to zero but less than or equal to 1.

In this embodiment, the Si—OAp compound can be fabricated with the Skelite™ synthetic biomaterial compound and together be shaped into a desired three-dimensional implant. Alternatively, the Si—OAp compound can be provided as a coating on a Skelite™ matrix or as a matrix dispersed therein. Alternatively, the Si—OAp compound may be intimately mixed with a granular or powdered form of Skelite™ for localized administration.

The Si—OAp compound of the invention as provided as a compound or composition can be formed into the appropriate configurations for use as a bone substitute by several methods. In one method, an organic material with open interstices such as a reticulated polyurethane foam is simply shaped to the desired configuration using ordinary cutting instruments, hot wire cutters, die cutters and the like. The configured foam material is used in any of the foregoing methods to produce the article of the invention. In another method, an organic foam such as that referred to earlier is coated with a ceramic slip and is heated to drive off solvent and convert the ceramic to the "green" state, at which point it can be shaped into the desired configuration. In a further method, the Si—OAp compound of the invention which has been fully sintered can be shaped by standard machining methods such as sawing and grinding, water jet or laser cutting, etc.

The silicon substituted oxyapatite compound (Si—OAp) of the invention has use in a variety of clinical conditions especially in the field of bone repair. The orthopedic surgeon is often faced with clinical situations in which bone has been removed, shattered or missing. Cancer surgery, accident trauma and genetic defects are frequently causes. Whenever this happens, and the remaining bone cannot be rejoined and stabilized in a satisfactory way, some sort of bone grafting is necessary. The need for bone grafts is the result of natural limitations for bone to repair itself. In the event of fractured or missing bone the remaining bone must be stabilized in its natural position by internal or external fixing methods, such as internal or external bone plates and plaster casts. This keeps the bone from moving so that the physiology of bone repair can occur; typically hematoma, fibrous callous, mineralized callous and remodeling. However, if much fragmentation has occurred or if too much bone is missing the bone does not reunite even if the remaining bone is stabilized. This typical non-union problem is one reason for considering bone grafts.

Historically, the best bone grafting material was natural bone (autogenous bone) from somewhere else in the patient. This is used where practical. Unfortunately, it is often impractical because of the unavailability of suitable bone in the patient. Even when it can be obtained from the patient there is still the trauma of removal of bone from somewhere else in the body, the danger of fracture at the removal site, and the danger a second surgical procedure. Therefore, a source of bone grafts from some other source is essential in many clinical situations.

If autogenous bone is not available the surgeon often uses bone from the same species but a different individual in that species (allograft bone). This causes problems with the immune system and brings with it danger of infection. The success rate is lower than that of autogenous bone. Because of these risks a bone grafting method has long been sought for these difficult clinical situations. Much research has been conducted to find new materials to replace natural bone. This includes the full spectrum of biocompatible metals, organics (plastics) and ceramics. None of these has been successful because, in general, the inert materials chosen for the purpose are either walled off by the foreign body mechanism of the host (a fibrous capsule around the implant) or have compromised physical performance due to degradation by dissolution. The Applicant's Skelite™ compound is one such successful material for bone graft as well as ex vivo tissue engineering products. It is now asserted that Si—OAp is another compound that may be used for such purpose.

In summary, a new silicon substituted oxyapatite (Si—OAp) bone biomaterial compound is provided and characterized such that it has clinical use as a synthetic biomaterial for orthopedic applications.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Methods of synthetic chemistry and organic chemistry referred to but not explicitly described in this disclosure and examples are reported in the scientific literature and are well known to those skilled in the art.

Example 1

Synthetic Preparation of Si—OAp

The Si—OAp compound can be made as a pure single phase using a similar process used to produce Skelite™ powders, however, the quantities of precursor reactants are specifically controlled in the mixture such that the ratio of Ca/(P+Si) is kept constant at about 1.67. The concentration of silicon must be sufficient to substantially remove $OH^-$ from the lattice, without causing the apatite structure to collapse to silicocarnotite ($Ca_5(PO_4)_2SiO_4$). The rearrangement of silicon during sintering to an equilibrium configuration, evenly distributed throughout the lattice allows oxygen, $O^{2-}$, to re-occupy the c-axis channel previously occupied by $OH^-$. The concentration of silicon required falls in a range between about 0.5 mol $SiO_2$: mol HA and about 1.5 mol $SiO_2$: mol HA, or 2.6 to 7.1 wt % silicon.

Preparation of Ca—P Colloidal Suspension (Sol-Gel)

The following procedure is for the preparation of sol-gel Si—OAp with approximately 2.6 wt % silicon (0.5 mol $SiO_2$: molHA). Solution A comprises a calcium nitrate tetrahydrate and Solution B comprises an ammonium dihydrogen orthophosphate (mono basic). Solution A is mixed with Solution B to produce the desired colloidal suspension. Solution A is prepared by adding 40 mls of doubly distilled water to 4.722 grams of calcium nitrate tetrahydrate, $Ca(NO_3)_2.4H_2O$. The solution is stirred at moderate speed for sufficient time to dissolve all of the calcium nitrate which is normally in the range of 3 minutes. To this solution, 3 mls of ammonia hydroxide ($NH_4OH$) is added and stirred for approximately another 3 minutes. To this solution is added 37 mls of double distilled water to provide a total solution volume of approximately 80 mls. The solution is stirred for another 7 minutes and covered. The pH of the solution is tested where a pH of about 11 is desired.

Solution B is prepared by adding 60 mls of double distilled water to a 250 ml beaker containing 1.150 grams of $NH_4H_2PO_4$. The beaker is covered and stirred at moderate speed for 3 to 4 minutes until all $NH_4H_2PO_4$ is dissolved. To this solution is added 71 mls of $NH_4OH$ and the beaker then covered and stirring continued for approximately another 7 minutes. To this is added another 61 mls of double distilled water and the beaker covered to provide a total solution volume of approximately 192 mls. The solution is then stirred for a further 7 minutes and covered. The pH of the solution is tested where a pH of about 11 is desired.

The desired sol-gel is then prepared by combining Solution B with Solution A. All of Solution A is introduced to a 500 ml reagent bottle. Stirring is commenced at a moderate speed and Solution B introduced to the reagent bottle at a rate of approximately 256 mls per hour until all 192 ml of Solution B is delivered into Solution A. An excess of Solution B may be prepared to compensate for any solution losses which may occur in the transfer process. After completion of this addition and combination of Solution A with Solution B, the resultant product is continued to be stirred at moderate speed for approximately 24 hours. The resultant colloidal suspension (sol-gel) is inspected for any abnormal precipitation or agglomeration. If any abnormal precipitation or agglomeration has occurred, the solution must be discarded and preparation commenced again. Approximately 240 mls of the colloidal suspension, that is the resultant sol-gel, is delivered to a centrifuge bottle and centrifuged for 20 minutes at about 500 rpm at room temperature. Following centrifugation, 180 mls of supernatant is discarded without disturbing the sediments. The sediments are gently resuspended by mixing in a smooth rotating manner for about 30 minutes.

Following the procedures for the formation and aging of the colloidal suspension, the colloid was processed to the stage of reducing the volume by centrifugation. 0.120 grams of silicon was added in the form of a finely divided (~10-100 nm) fumed silica colloid (Cab-o-sperse A1695™ obtained from Cabot Corporation, 500 Commerce Drive, Aurora Ill. 60504). The precipitate with introduced silicon was dried for approximately 5 hours at 100° C. and sintered for one hour under vacuum at $10^{-5}$ torr. Pressures of between about $5\times10^{-4}$ torr to $1\times10^{-5}$ torr can be used) at a temperature of 1175° C. A fine powder was formed through mechanical grinding of the sintered material in a motorized mortar and pestle (Retsch Model RM100 USA). The presence of the additive within the sintered ceramics was checked by wet chemical analysis.

The preceding sintering process may be carried out in standard laboratory vacuum furnaces of various sizes, capable of operating at temperatures from ambient up to at least 1200° C., and designed to maintain accurate and stable internal temperatures, such asbetween 800° C. and 1200° C. and any range therebetween such as for example 1000° C. to about 1200° C.

In accordance with this process a fine or coarse powder, pellets, three-dimensional shaped pieces, macroporous structures, thin films and coatings of the biomaterial compound can be produced on a consistent basis having the desired composition where variability in the various processing parameters have been minimized to ensure such consistency.

Although preferred embodiments have been described herein in detail, it is understood by those skilled in the art that variations may be made thereto without departing from the scope of the invention.

What is claimed is:

1. A silicon substituted oxyapatite compound (Si—OAp), wherein said compound has the formula $Ca_5(PO_4)_{3-x}(SiO_4)_xO_{(1-x)/2}$, where $0<x<1.0$ and wherein said compound is a synthetic bone biomaterial that is biocompatible in vivo.

2. The compound of claim 1, wherein said compound is provided as a fine or coarse powder, pellets, paste, three-dimensional shaped pieces, macroporous and microporous structures, thin films and coatings.

3. The compound of claim 2, wherein said compound is mixed with one or more calcium phosphate compounds selected from the group consisting of oxyapatite, silicon substituted α-tricalcium phosphate, hydroxyapatite, calcium hydroxyapatite, tricalcium phosphate, calcium oxide, alpha-tricalcium phosphate and beta-tricalcium phosphate.

4. The compound of claim 3, wherein said compound is mixed with silicon substituted α-tricalcium phosphate.

5. The compound of claim 1, wherein said compound is further provided with an agent selected from the group consisting of calcium carbonate, calcitonin preparations, sex hormones, prostaglandin A1, bisphosphonic acids, ipriflavones, fluorine compounds, vitamin K, bone morphogenetic proteins (BMPs), fibroblast growth factor (FGF), platelet-derived growth factor (PDGF), transforming growth factor (TGF-β), insulin-like growth factors 1 and 2 (IGF-1, 2), endothelin, parathyroid hormone (PTH), epidermal growth factor (EGF), leukemia inhibitory factor (LIP), osteogenin, BCSP, bone resorption repressors and mixtures thereof.

6. The compound of claims 1, wherein said compound additionally comprises a bioresorbable polymer.

7. The compound of claim 6, wherein said bioresorbable polymer is selected from the group consisting of collagen, poly-lactic acid, poly-glycolic acid, copolymers of lactic acid and glycolic acid, chitosan, chitin, gelatin and mixtures thereof.

8. The compound of claim 7, wherein said bioresorbable polymer material is reinforced with a particulate form of the Si—OAp compound or a silicon substituted α-tricalcium phosphate compound.

9. A composition to promote bone repair and bone growth, said composition comprising a silicon substituted oxyapatite compound (Si—OAp), wherein said compound has the formula $Ca_5(PO_4)_{3-x}(SiO_4)_xO_{(1-x)/2}$, where $0<x<1.0$ and wherein said compound is a synthetic bone biomaterial.

10. The composition of claim 9, wherein said compound is provided as a fine or coarse powder, pellets, paste, three-dimensional shaped pieces, macroporous and microporous structures, or thin films and coatings.

11. The composition of claim 9, wherein said compound is mixed with one or more calcium compounds selected from the group consisting of silicon substituted α-tricalcium phosphate, oxyapatite, hydroxyapatite, calcium hydroxyapatite, tricalcium phosphate, calcium oxide, alpha-tricalcium phosphate and beta-tricalcium phosphate.

12. The composition of claim 11, wherein said compound is mixed with silicon substituted α-tricalcium phosphate.

13. The composition of claim 9, wherein said composition further comprises an agent selected from the group consisting of calcium carbonate, calcitonin preparations, sex hormones, prostaglandin A1, bisphosphonic acids, ipriflavones, fluorine compounds, vitamin K, bone morphogenetic proteins (BMPs), fibroblast growth factor (FGF), platelet-derived growth factor (PDGF), transforming growth factor (TGF-β), insulin-like growth factors 1 and 2 (IGF-1, 2), endothelin, parathyroid hormone (PTH), epidermal growth factor (EGF), leukemia inhibitory factor (LIP), osteogenin, BCSP, bone resorption repressors and mixtures thereof.

14. The composition of claim 9, wherein said composition additionally comprises a bioresorbable polymer.

15. The composition of claim 14, wherein said bioresorbable polymer is selected from the group consisting of collagen, poly-lactic acid, poly-glycolic acid, copolymers of lactic acid and glycolic acid, chitosan, chitin, gelatin and mixtures thereof.

16. The composition of claim 15, wherein said bioresorbable polymer material additionally comprises a particulate form of the Si—OAp compound or a silicon substituted α-tricalcium phosphate compound.

17. A method for making a silicon substituted oxyapatite of the formula $Ca_5(PO_4)_{3-x}(SiO_4)_xO_{(1-x)/2}$, where $0<x<1.0$, said method comprising: mixing a calcium phosphate colloidal suspension with a finely dispersed, fumed silica; while maintaining a ratio of Ca/(P+Si) at about 1.67 in said mixture; and sintering for about 1 hour at a temperature of about 800° C. to about 1200° C. under vacuum.

18. The method of claim 17, wherein said temperature is about 1000° C. to about 1200° C.

19. The method of claim 18, wherein said temperature is about 1175° C.

20. The method of claim 17, wherein said vacuum is about $5\times/0^{-4}$ torr to about $1\times10^{-5}$ torr.

21. The method of claim 17, wherein said silicon is provided at a concentration of between about 0.5 mol $SiO_2$: mol HA to about 1.5 mol $SiO_2$: mol HA.

22. The method of claim 17, wherein said silicon is provided at a concentration of about 2.6 to 7.1 wt % silicon.

23. A method for the treatment of bone-related clinical conditions selected from the group consisting of an orthopedic, maxillo-facial and dental defect, the method comprising providing a silicon substituted oxyapatite compound (Si—OAp) of claim 1 wherein the compound is provided to said defect as a fine or coarse powder, pellets, three-dimensional shaped pieces, macroporous structures, thin films and coatings.

24. A method for substituting natural bone at sites of skeletal surgery in human and animal hosts with a silicon substituted oxyapatite compound (Si—OAp), wherein said compound has the formula $Ca_5(PO_4)_{3-x}(SiO_4)_xO_{(1-x)/2}$, where $0<x<1.0$, the method comprising the steps of: implanting said Si—OAp compound at the site of skeletal surgery wherein such implantation promotes the formation of new bone tissue at the interfaces between the compound and said host.

25. The method of claim 23, wherein said compound is provided as a fine or coarse powder, pellets, paste, three-dimensional shaped pieces, macroporous and microporous structures, thin films and coatings.

26. The method of claim 23, wherein said compound is mixed with one or more calcium compounds selected from the group consisting of oxyapatite, a silicon substituted α-tricalcium phosphate, hydroxyapatite, calcium hydroxyapatite, tricalcium phosphate, calcium oxide, alpha-tricalcium phosphate and beta-tricalcium phosphate.

27. The method of claim 23, wherein said compound is further provided with an agent selected from the group consisting of calcium carbonate, calcitonin preparations, sex hormones, prostaglandin A1, bisphosphonic acids, ipriflavones, fluorine compounds, vitamin K, bone morphogenetic proteins (BMPs), fibroblast growth factor (FGF), platelet-derived growth factor (PDGF), transforming growth factor (TGF-β), insulin-like growth factors 1 and 2 (IGF-1, 2), endothelin, parathyroid hormone (PTH), epidermal growth factor (EGF), leukemia inhibitory factor (LIP), osteogenin, BCSP, bone resorption repressors and mixtures thereof.

28. The method of claim 23, wherein said compound additionally comprises a bioresorbable polymer.

29. The method of claim 28, wherein said bioresorbable polymer is selected from the group consisting of collagen, poly-lactic acid, poly-glycolic acid, copolymers of lactic acid and glycolic acid, chitosan, chitin, gelatin and mixtures thereof.

30. The method of claim 28, wherein said bioresorbable polymer material is reinforced with a particulate form of the Si—OAp compound, a and/or a silicon substituted α-tricalcium phosphate compound compound.

* * * * *